United States Patent
Nayfeh et al.

(10) Patent No.: US 10,072,991 B2
(45) Date of Patent: Sep. 11, 2018

(54) LANTHANIDE AND SILICON-BASED NANOPARTICLE PRESSURE SENSOR AND SYSTEM

(71) Applicant: The United States of America as Represented by The Secretary of The Army, Washington, DC (US)

(72) Inventors: Munir H. Nayfeh, Urbana, IL (US); Charles P. Marsh, Urbana, IL (US); Ghassan K. Al-Chaar, Champaign, IL (US)

(73) Assignee: The United States of America as Represented by The Secretary of The Army, Washington, DC (US)

( * ) Notice: Subject to any disclaimer, the term of this patent is extended or adjusted under 35 U.S.C. 154(b) by 0 days.

(21) Appl. No.: 15/073,406

(22) Filed: Mar. 17, 2016

(65) Prior Publication Data
US 2017/0268943 A1    Sep. 21, 2017

(51) Int. Cl.
G01B 11/16      (2006.01)
G01L 1/24       (2006.01)
G01N 21/70      (2006.01)

(52) U.S. Cl.
CPC .............. *G01L 1/24* (2013.01); *G01N 21/70* (2013.01)

(58) Field of Classification Search
CPC ............ G01L 1/24; G01N 21/70; G01B 11/16
USPC ........................................................ 73/800
See application file for complete search history.

(56) References Cited

U.S. PATENT DOCUMENTS

| | | | | |
|---|---|---|---|---|
| 6,456,423 B1* | 9/2002 | Nayfeh | ................. | B82Y 20/00 324/97 |
| 7,200,318 B2* | 4/2007 | Banin | .................... | C09K 11/02 257/42 |
| 8,071,181 B2* | 12/2011 | Hegmann | ............ | B01J 13/0043 252/299.01 |
| 8,314,475 B2* | 11/2012 | Ribeiro | ................... | H01L 45/14 257/30 |
| 9,529,228 B2* | 12/2016 | Banin | ............... | G02F 1/133617 |
| 9,700,940 B2* | 7/2017 | Zinn | ..................... | B22F 1/0007 |
| 2005/0169831 A1* | 8/2005 | Montgomery | ......... | B82Y 30/00 423/447.1 |
| 2011/0088739 A1* | 4/2011 | Zinn | ..................... | B82Y 30/00 136/205 |
| 2014/0227548 A1* | 8/2014 | Myrick | ................... | C06B 45/30 428/570 |

* cited by examiner

*Primary Examiner* — Harshad R Patel
*Assistant Examiner* — Octavia Hollington
(74) *Attorney, Agent, or Firm* — Brian C. Jones

(57) ABSTRACT

A nanoparticle sensor apparatus includes a silicon-based nanoparticle having a centrosymmetric crystalline structure. A lanthanide atom embedded within the silicon-based nanoparticle provides light emission when the sensor apparatus undergoes pressure loading. This sensor apparatus may be encapsulated in a polymer matrix to form a nanoparticle sensor matrix apparatus which may be located on or in a structure. To measure the pressure on such a structure, a UV light source illuminates the sensor apparatus. An optical emission detector detects the intensity of light emitted from the sensor in response, while a processor correlates that intensity to the pressure loading.

20 Claims, 2 Drawing Sheets

LANTHANIDE AND SILICON-BASED NANOPARTICLE PRESSURE SENSOR AND SYSTEM

STATEMENT OF GOVERNMENT INTEREST

The invention described herein was made by an employee of the United States Government and which may be manufactured and used by the Government of the United States of America for governmental purposes without the payment of any royalties thereon or therefore.

BACKGROUND

1. Field of Invention

This invention relates to the field of nanotechnology, and more specifically to a nanoparticle.

2. Description of the Related Art

High-pressure sensors are used by material scientists to measure localized material response to "pressure loading" events such as shocks, explosions, and the application of pressure by gas-guns and lasers. Data from the high-pressure sensors is used to determine pressure at multiple points or sampling distances. High-pressure sensors have a "spatial resolution," which refers to the number of sample points per unit of surface area. The higher the number of sample points, the higher the degree of spatial resolution.

The difficulty of achieving a high degree of spatial resolution over a large surface area, such as a bridge or a building, is a problem known in the art. In such cases, the only available data may be global information for the entire system, which does not give scientists insight as to location of pressure on a system or pressure on a single component. Currently, scientists must use heavy computational simulations to attain a high level of any spatial resolution to assess localized conditions.

Some prior art pressure sensor systems use Raman scattering in silica nanoparticles. In bulk silica, pressure produces densification, which is used as a signature of the pressure. However, using silica nanoparticles to measure pressure requires complex spectroscopic procedures to examine the silica nanoparticles and calculate the pressure.

Another sensor scheme uses Y2O3:Eu3+ nanoparticles. Yttrium-based nanoparticles have been tested under the pressure of up to 78 kbar at room temperature. However, Yttrium-based nanoparticles require a rare element, one known to be toxic. Moreover, the behavior of Yttrium-based nanoparticles at higher pressures up to 300 kbar is unknown, making their utility for high-pressure application uncertain.

There is an unmet need for the capability to probe localized material response to pressure without resorting to complex spectroscopic procedures.

There is a further unmet need for an in-situ pressure sensing capability that does not present a health or environmental hazard and covers a wide range of pressures.

SUMMARY OF THE INVENTION

In one embodiment of the invention, a nanoparticle sensor apparatus includes a silicon-based nanoparticle having a centrosymmetric crystalline structure and a plurality of bonding sites. A lanthanide atom is embedded within the silicon-based nanoparticle.

In another embodiment of the invention, a nanoparticle sensor matrix apparatus includes at least one nanoparticle sensor, as above, encapsulated in at least one polymer matrix.

In another embodiment of the invention, a nanoparticle-based sensor system includes at least one nanoparticle sensor matrix apparatus, as above, a UV light source producing UV light having a wavelength between 10 nm and 400 nm, a UV detector in line with the UV light source, a lens collimator in line with the UV light source, an optical emission detector and a data processor operatively connected to the optical emission detector.

TERMS OF ART

As used herein, the term "lanthanide" means the series of metallic elements consisting of Cerium, Dysprosium, Erbium, Europium, Gadolinium, Holmium, Lanthanum, Lutetium, Neodymium, Praseodymium, Promethium, Samarium, Terbium, Thulium and Ytterbium.

As used herein, the term "solid shape" means the configuration of a discrete three-dimensional solid.

DETAILED DESCRIPTION OF INVENTION

Figure 1:
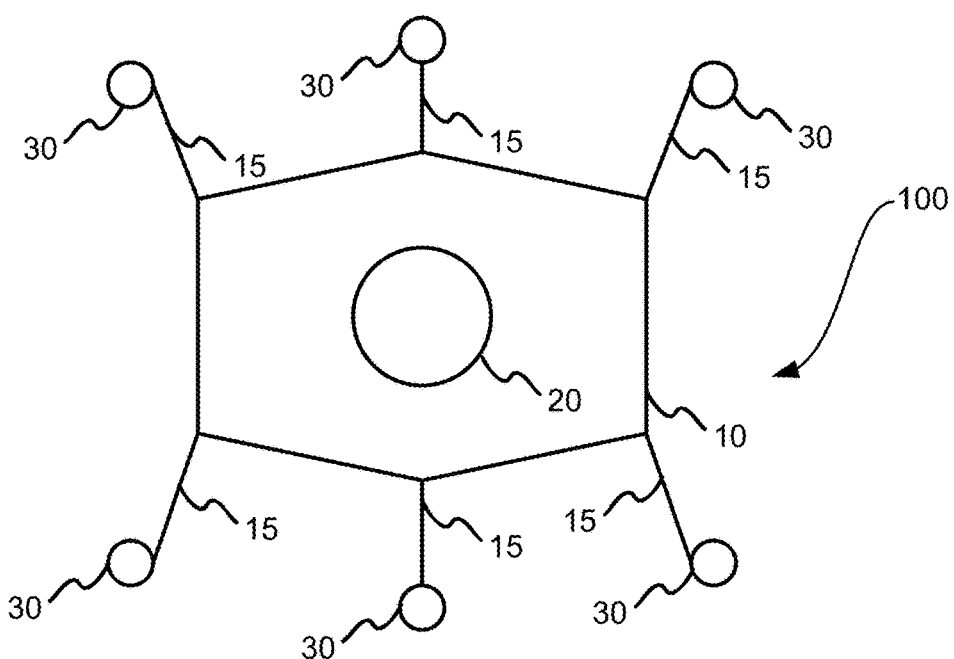
FIG. 1 illustrates an exemplary embodiment of a nanoparticle sensor.

FIG. 1 illustrates an exemplary embodiment of a nanoparticle sensor 100. Nanoparticle sensor 100 includes a silicon-based nanoparticle 10 with an implanted lanthanide atom 20 and optional hydrogen atoms 30.

In the exemplary embodiment, silicon-based nanoparticle 10 includes a plurality of bonding sites 15. Silicon-based nanoparticle 10 is made of approximately 29 silicon atoms arranged in a centrosymmetric configuration. In various embodiments, silicon-based nanoparticle 10 may have a diameter of approximately 1 nm to approximately 10 nm. The small size of silicon-based nanoparticle 10, combined with low volume fractions, limits the influence of nanoparticle sensor 100 on the high-pressure phenomena studied while still allowing for high spatial resolution of the peak local pressure. The use of silicon is critical, as it avoids toxic side effects during and after use, and is a widely available and relatively inexpensive material.

Lanthanide atom 20 embeds within and dopes silicon-based nanoparticle 10. Lanthanide atoms provide little optical activity prior to application of an external force. In one embodiment, lanthanide atom 20 is an Erbium (Er) atom. Since Er does not exhibit light emission in the absence of pressure, it avoids the measurement of a small change in the parameters of interest and provides a better signal with a larger signal to noise ratio. In one embodiment, incubation of silicon-based nanoparticle 10 in a solution of lanthanide salt embeds lanthanide atom 20. In the exemplary embodiment, incubation in an erbium chloride ($ErCl_3$) solution embeds Er atoms. Another embodiment bombards a film of silicon-based nanoparticles 10 with lanthanide atoms such as, but not limited to, fast $Er^{+3}$ atoms.

A host with a centrosymmetric crystalline structure, such as silicon-based nanoparticle 10, has a symmetry that cannot activate light emissions in lanthanide atom 20. However, upon application of pressure, the strain induced in silicon-based nanoparticle 10 will distort its surface, breaking the centrosymmetry. This allows the crystal field of silicon-based nanoparticle 10 to introduce admixtures of opposite parity interactions that "turn on" light emission in lanthanide atom 20. Monitoring the light emitted from lanthanide atom 20 and correlating the intensity of emission with pressure allows pressure measurement.

However, the bulk of experimental evidence supports the idea that free lanthanide atoms have insignificant light emission, unusable for pressure measurement. The optical absorption and emission transitions in free lanthanides are very weak because they are forbidden according to quantum theory. The oscillator strength of these transitions is of the order of 10^6. One-photon lanthanides intensities in the 4f-4f manifold are inhibited. Electric quadruple transitions are predicted to be even weaker and have not yet been observed. This use of lanthanide atom 20 in nanoparticle sensor 100 is therefore the result of unexpected experimental results.

In one embodiment, optional hydrogen atoms 30 attach to bonding sites 15 on silicon-based nanoparticle 10. In alternate embodiments, ligands with longer chains attach to bonding sites 15 to embed silicon-based nanoparticle 10 within an external material. This enables external material to transfer pressure to the structure of silicon-based nanoparticle 10.

Figure 2:
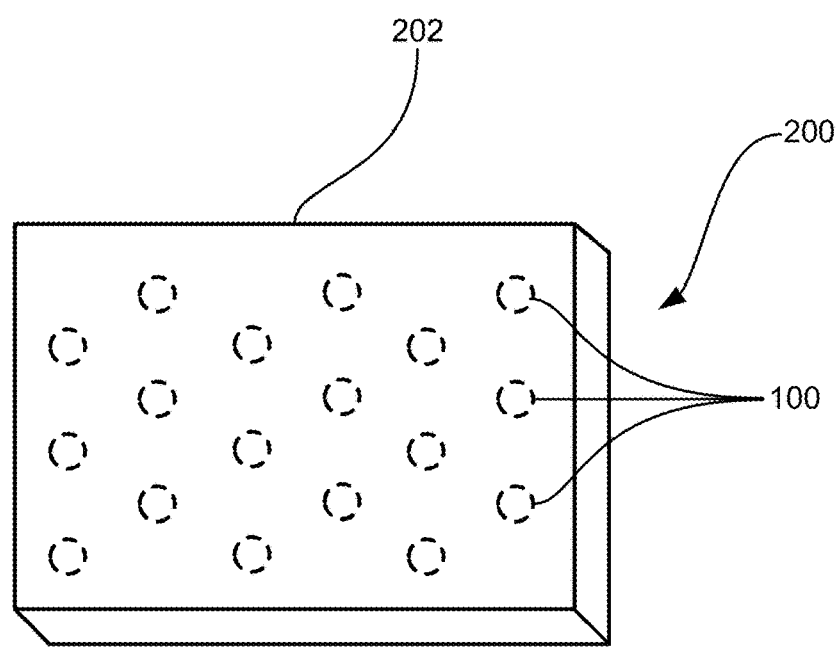
FIG. 2 illustrates an exemplary embodiment of a sensor matrix.

FIG. 2 illustrates an exemplary embodiment of a nanoparticle sensor matrix 200. Nanoparticle sensor matrix 200 includes at least one nanoparticle sensor 100 encapsulated by a polymer matrix 202. In the exemplary embodiment, nanoparticle sensor matrix 200 takes the form of a cuboid solid shape. In other embodiments, solid shapes may include, but are not limited to, a prism, a cube, a cylinder, a pyramid, a cone, a disk, a sphere or any combination thereof. In another embodiment, nanoparticle sensor matrix 200 takes the form of multiple solid shapes. In another embodiment, nanoparticle sensor matrix 200 takes the form of a coating on an object or structure. This coating has a thickness of approximately 1 nm to approximately 4 µm. In one embodiment, coating an object involves spraying from a nanoparticle colloid. In one embodiment, coating an object involves incubating the object in a nanoparticle colloid.

In one embodiment, at least one nanoparticle sensor 100 is a single nanoparticle sensor 100. In another embodiment, at least one nanoparticle sensor 100 is a plurality of nanoparticle sensors 100. These nanoparticle sensors 100 may form a two-dimensional array or a three-dimensional array. In various embodiments, distribution of nanoparticle sensors 100 may be randomly distributed throughout polymer matrix 202, uniform throughout polymer matrix 202, uniform in at least one section of polymer matrix 202, uniform in multiple sections of polymer matrix 202, uniform in multiple sections of polymer matrix 202 in differing concentrations or on a gradient. Nanoparticle sensors 100 may also form predetermined patterns within polymer matrix 202. Space between nanoparticle sensors 100 may range from approximately 3 nm to approximately 10 m.

Polymer matrix 202 is a polymer such as, but not limited to, room temperature vulcanization silicone (RTV), epoxy, or Poly(methyl methacrylate) (PMMA). Polymers making up polymer matrix 202 must have sufficient light transmission to allow external visualization of light emitted from at least one nanoparticle sensor 100. Such polymers may have a light transmittance of between approximately 80% to approximately 93%. Polymers making up polymer matrix 202 must also have sufficient resistance to deformation to transmit pressure to at least one nanoparticle sensor 100. Such polymers may have a Young's modulus of between approximately 1 $GN/m^2$ to approximately 4 $GN/m^2$.

In one embodiment, nanoparticle sensor matrix 200 embeds in a structure or object. In another embodiment, nanoparticle sensor matrix 200 coats a surface of a structure or object. Nanoparticle sensor matrix 200 has a wide range of potential applications. For instance, the strain-induced variations in the luminescence of nanoparticle sensor 100 can be used to develop on-line diagnostics of the health of infrastructure of importance to the military by embedding the particles in the structures. The embedded shapes or coatings of nanoparticle sensor matrix 200 can enable and facilitate rapid non-destructive inspection and health monitoring of infrastructure and machines. Other applications include evaluating shocks, as well as high explosive, gas-gun and laser-driven events.

Figure 3:
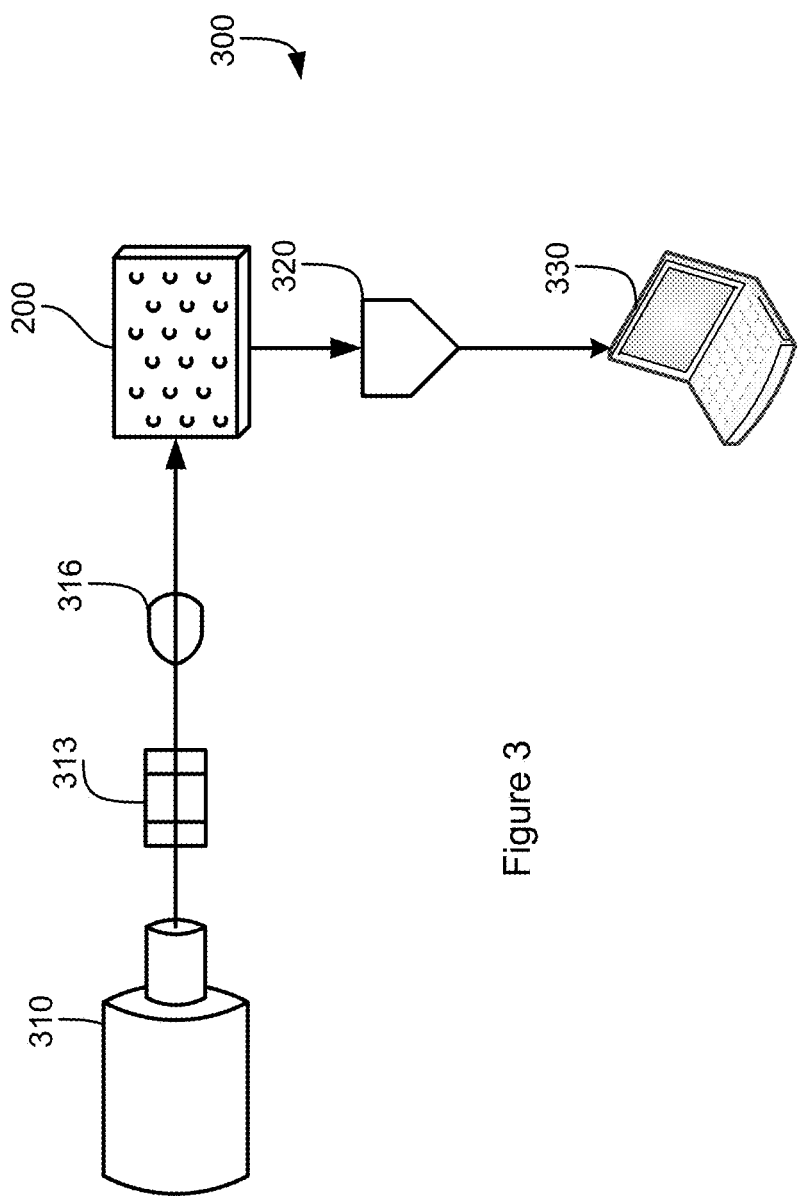
FIG. 3 illustrates an exemplary embodiment of a sensor system.

FIG. 3 illustrates an exemplary embodiment of a sensor system 300. Sensor system 300 includes an ultraviolet (UV) light source 310, a UV detector 313, a lens collimator 316 and an optical emission detector 320 operatively coupled to a data processor 330. The medium to be examined includes at least one nanoparticle sensor matrix 200. The interfaced optical measuring and electronics of sensor system 300 allow recording of the local peak pressure.

UV light source 310 transmits UV light at a wavelength of between 10 nm and 400 nm and is in line, optically, with UV detector 313 and lens collimator 316. UV detector 313 detects transmission of the UV light to ensure that a malfunction in UV light source 310 does not result in a false negative reading. Lens collimator 316 collimates the UV light to ensure even illumination of nanoparticle sensor matrix 200.

When collimated UV light illuminates nanoparticle sensor matrix 200, at least one nanoparticle sensor 100 emits light. Optical emission detector 320 detects this resultant light emission and converts the detected data to a digital format. In one embodiment, optical emission detector 320 stores the digital data. In another embodiment, optical emission detector 320 transmits the digital data to data processor 330 for processing. In certain embodiments, this may be real-time transmission. In one embodiment, optical emission detector 320 is a wide-spectrum spectrometer. In another embodiment, optical emission detector 320 is an optical bandpass detector.

Sensor system 300 employs at least one nanoparticle sensor 100 that displays an emission intensity that is proportional to the pressure loading of nanoparticle sensor 100 under UV light illumination. As previously mentioned, one embodiment includes at least one nanoparticle sensor 100 in nanoparticle sensor matrix 200 coated or layered onto a structure so as to render the structure "self-sensing" with respect to stress. Inspection of a bridge or a critical machine part, for example, becomes a matter of UV illumination and measure of emitted intensity. In one embodiment, this process is automated.

It will be understood that many additional changes in the details, materials, procedures and arrangement of parts, which have been herein described and illustrated to explain the nature of the invention, may be made by those skilled in the art within the principle and scope of the invention as expressed in the appended claims.

It should be further understood that the drawings are not necessarily to scale; instead, emphasis has been placed upon illustrating the principles of the invention. Moreover, the term "approximately" as used herein may be applied to modify any quantitative representation that could permissibly vary without resulting in a change in the basic function to which it is related.

What is claimed is:

1. A nanoparticle pressure sensor apparatus, comprised of: a silicon-based nanoparticle comprising a centrosymmetric crystalline structure and a plurality of bonding sites; and a lanthanide atom embedded within said silicon-based nanoparticle, wherein said nanoparticle pressure sensor apparatus displays an emission intensity that is proportional to a pressure loading of said sensor under UV illumination.

2. The apparatus of claim 1, wherein said silicon-based nanoparticle comprises approximately 29 silicon atoms.

3. The apparatus of claim 1, wherein said silicon-based nanoparticle has a spherical diameter between approximately 1 nm and approximately 10 nm.

4. The apparatus of claim 1, wherein said lanthanide atom is an Erbium atom.

5. A nanoparticle pressure sensor matrix apparatus, comprised of: at least one nanoparticle sensor, wherein said at least one nanoparticle sensor comprises: a silicon-based nanoparticle having a centrosymmetric crystalline structure; and a lanthanide atom embedded in said silicon-based nanoparticle; and at least one polymer matrix encapsulating said at least one nanoparticle sensor, wherein said nanoparticle pressure sensor matrix apparatus displays an emission intensity that is proportional to a pressure loading of said sensor under UV illumination.

6. The apparatus of claim 5, wherein said at least one nanoparticle sensor comprises a plurality of nanoparticle sensors.

7. The apparatus of claim 6, wherein said plurality of nanoparticle sensors are randomly distributed though said at least one polymer matrix.

8. The apparatus of claim 6, wherein said plurality of nanoparticle sensors are arranged in a two-dimensional array.

9. The apparatus of claim 6, wherein said plurality of nanoparticle sensors are arranged in a three-dimensional array.

10. The apparatus of claim 6, wherein said plurality of nanoparticle sensors are uniformly distributed throughout said at least one polymer matrix.

11. The apparatus of claim 6, wherein said plurality of nanoparticle sensors are uniformly distributed within at least one section of said at least one polymer matrix.

12. The apparatus of claim 6, wherein said plurality of nanoparticle sensors are distributed in a pattern in said at least one polymer matrix.

13. The apparatus of claim 6, wherein said plurality of nanoparticle sensors are distributed in a gradient in said at least one polymer matrix.

14. The apparatus of claim 6, wherein said plurality of nanoparticle sensors are spaced approximately 3 nm to approximately 10 m apart.

15. The apparatus of claim 5, wherein said at least one polymer matrix forms a three-dimensional shape.

16. The apparatus of claim 5, wherein said at least one polymer matrix forms a coating attached to a surface of an object.

17. The apparatus of claim 16, wherein said coating is approximately 1 nm to approximately 4 μm thick.

18. The apparatus of claim 5, wherein said at least one polymer matrix comprises a polymer having a light transmittance of between approximately 80% to approximately 93%.

19. The apparatus of claim 5, wherein said at least one polymer matrix comprises a polymer having a Young's modulus of between approximately 1 $GN/m^2$ to approximately 4 $GN/m^2$.

20. A nanoparticle-based pressure sensor system, comprised of: at least one nanoparticle pressure sensor matrix apparatus, comprised of: at least one nanoparticle pressure sensor, wherein said at least one nanoparticle pressure sensor comprises: a silicon-based nanoparticle having a centrosymmetric crystalline structure, and a lanthanide atom embedded in said silicon-based nanoparticle, and at least one polymer matrix encapsulating said at least one nanoparticle pressure sensor; a UV light source producing UV light having a wavelength between 10 nm and 400 nm; a UV detector in line with said UV light source; a lens collimator in line with said UV light source; an optical emission detector, and a data processor operatively connected to said optical emission detector, wherein said nanoparticle pressure sensor apparatus displays an emission intensity that is proportional to a pressure loading of said sensor under UV illumination.

* * * * *